United States Patent [19]

Mausner

[11] Patent Number: 5,391,373
[45] Date of Patent: Feb. 21, 1995

[54] SKIN CREAM COMPOSITION

[75] Inventor: Jack Mausner, New York, N.Y.

[73] Assignee: Chanel, Inc., New York, N.Y.

[21] Appl. No.: 907,487

[22] Filed: Jul. 1, 1992

[51] Int. Cl.$^6$ .............................................. A61K 7/48
[52] U.S. Cl. .................................. 424/401; 424/195.1;
514/78; 514/777; 514/783; 514/784; 514/785;
514/844; 514/846; 514/847; 514/873
[58] Field of Search ................. 424/401, 450, 195.1;
514/783, 78, 777, 784, 785, 844, 846, 847, 873

[56] References Cited

U.S. PATENT DOCUMENTS

| | | | |
|---|---|---|---|
| 3,697,643 | 10/1972 | Shephard et al. | 424/63 |
| 3,864,275 | 2/1975 | Kan et al. | 252/316 |
| 3,911,105 | 10/1975 | Papantoniou et al. | 424/64 |
| 3,966,398 | 6/1976 | Vanlerberghe et al. | 8/11 |
| 4,125,549 | 11/1978 | Coopersmith et al. | 260/425 |
| 4,247,411 | 1/1981 | Vanlerberghe et al. | 252/316 |
| 4,369,037 | 1/1983 | Matsunaga et al. | 8/127.51 |
| 4,400,295 | 8/1983 | Ootsu et al. | 252/356 |
| 4,423,031 | 12/1983 | Murui et al. | 424/63 |
| 4,460,371 | 7/1984 | Abber | 604/897 |
| 4,481,186 | 11/1984 | Deckner | 424/59 |
| 4,549,990 | 10/1985 | Seguin et al. | 260/397.25 |
| 4,608,392 | 8/1986 | Jacquet et al. | 514/844 |
| 4,752,496 | 6/1988 | Fellows et al. | 427/27 |
| 4,758,599 | 7/1988 | Minetti | 514/844 |
| 4,820,510 | 4/1989 | Arraudeau et al. | 424/63 |
| 4,883,659 | 11/1989 | Goodman et al. | 424/78 |
| 4,925,667 | 5/1990 | Fellows et al. | 424/401 |
| 4,927,952 | 5/1990 | Gueyne et al. | 556/419 |
| 4,952,560 | 8/1990 | Kigasawa et al. | 514/2 |
| 4,980,155 | 12/1990 | Shah et al. | 424/63 |
| 4,988,502 | 1/1991 | Ounanian et al. | 424/63 |
| 5,034,226 | 7/1991 | Beck | 424/195.1 |
| 5,037,803 | 8/1991 | Gueyne et al. | 514/2 |
| 5,053,220 | 10/1991 | Arraudeau et al. | 424/63 |
| 5,053,221 | 10/1991 | Robertson et al. | 424/63 |
| 5,061,481 | 10/1991 | Suzuki et al. | 424/63 |
| 5,215,759 | 6/1993 | Mausner | 424/489 |
| 5,254,331 | 10/1993 | Maunser | 424/59 |

*Primary Examiner*—G. S. Kishore
*Assistant Examiner*—Jyothsna Venkat
*Attorney, Agent, or Firm*—Merchant & Gould

[57] ABSTRACT

A skin cream composition according to the present invention provides significant retexturization of the skin, producing significantly improved smoothness, as well as significantly minimizing age spots and improving color of the skin, together with increasing the firmness and moisture content of the skin. The composition can comprise: water, and emulsified and dispersed in the water: (1) sodium lactate; (2) a micellar complex comprising horse chestnut extract, Crataegus extract, water, panthenol, propylene glycol, phospholipids, phenoxyethanol, glycosphingolipids, chlorphenesin, and cholesterol; (3) a protein complex comprising serum proteins, hydrolyzed animal proteins, and glycogen; (4) a carbohydrate-based complex comprising dextran, glycine, and glucosamine; (5) a long-chain fatty acid ester of retinol; (6) a long-chain fatty acid ester of ascorbic acid; and (7) a short-chain fatty acid ester of tocopherol. The sodium lactate, the micellar complex, the protein complex, the carbohydrate-based complex, the retinol ester, the ascorbic acid ester, and the tocopherol ester are each present in a quantity sufficient to significantly increase the smoothness and/or firmness of skin to which the composition is applied, as well as significantly minimizing age spots and improving color. The composition can optionally contain other cosmetic components, such as (1) a complex of cyclomethicone and dimethiconol; (2) an aqueous solution of sodium hyaluronate; (3) glycosaminoglycans; and (4) a lipid complex comprising phospholipids, sphingolipids, and octyldodecanol, as well as ancillary components.

3 Claims, No Drawings

SKIN CREAM COMPOSITION

BACKGROUND

This application is directed to an improved skin cream composition.

Modern environmental conditions, such as heating and air conditioning, exposure to the sun, and environmental pollution exert severe stress on the skin and accelerate the natural aging process, resulting in wrinkles, loss of firmness and elasticity, age spots, discoloration, dryness, and other cosmetically undesirable effects. Although a number of skin cream compositions already exist, there is a need for a simple to apply and effective all-in-one cosmetic treatment, such as a skin cream, that can retexturize the skin, increase its firmness, color, and smoothness, while increasing its moisture content to overcome drying caused by the environment.

SUMMARY

I have developed a skin cream composition incorporating a new combination of ingredients. The skin cream composition of the present invention simultaneously promotes significant retexturizing of the skin, significantly increasing its smoothness, improving its color, while also increasing its firmness and moisture content.

In general, a skin cream composition according to the present invention comprises: water, and emulsified and dispersed in the water:

(1) sodium lactate;
(2) a complex comprising horse chestnut extract, phospholipids, and glycosphingolipids;
(3) a complex comprising serum proteins and glycogen;
(4) a carbohydrate-based complex comprising dextran, glycine, and glucosamine;
(5) a long-chain fatty acid ester of retinol;
(6) a long-chain fatty acid ester of ascorbic acid; and
(7) a short-chain carboxylic acid ester of tocopherol.

The sodium lactate, the complex comprising horse chestnut extract, phospholipids, and glycosphingolipids, the complex comprising serum proteins and glycogen, the carbohydrate-based complex, the retinol ester, the ascorbic acid ester, and the tocopherol ester are each present in a quantity sufficient to increase the smoothness, color, and/or firmness of skin to which the composition is applied. These ingredients further act to minimize age spots. They comprise the cosmetic components.

Preferably, the complex comprising horse chestnut extract, phospholipids, and glycosphingolipids is a micellar complex further comprising Crataegus extract, water, panthenol, propylene glycol, phenoxyethanol, chlorphenesin, and cholesterol.

Preferably, the complex comprising serum proteins and glycogen further comprises hydrolyzed animal proteins. More preferably, the complex further comprises sodium lactate, sodium pyrrolidone carboxylate, and glycerol in addition to hydrolyzed animal proteins.

Preferably, the skin cream composition can further comprise at least one of the following additional, optional, cosmetic components:

(1) a complex of cyclomethicone and dimethiconol;
(2) an aqueous solution of sodium hyaluronate;
(3) glycosaminoglycans;
(4) a lipid complex comprising phospholipids, sphingolipids, and octyldodecanol.

Most preferably, the composition comprises all four of these optional cosmetic components.

In a preferable cosmetic composition of the present invention, the sodium lactate comprises from about 4.25% to about 5.75% of the composition, the micellar complex comprises from about 2.5% to about 3.5% of the composition, the protein complex comprises from about 2.5% to about 3.5% of the composition, the carbohydrate-based complex comprises from about 0.0001% to about 0.1% of the composition, the retinol ester comprises from about 0.05% to about 0.15% of the composition, the ascorbic acid ester comprises from about 0.01% to about 0.02% of the composition, the tocopherol ester comprises from about 0.4% to about 0.6% of the composition, the complex of cyclomethicone and dimethiconol comprises from about 0.0001% to about 0.1% of the composition, the aqueous solution of sodium hyaluronate is about 1% by weight and comprises from about 3.4% to about 4.6% of the composition, the glycosaminoglycans comprise from about 2% to about 6% of the composition, and the lipid complex comprises from about 2% to about 5% of the composition.

The retinol ester can be selected from the group consisting of retinyl palmitate, retinyl myristate, and retinyl stearate. Preferably, the retinol ester is retinyl palmitate.

The ascorbic acid ester can be ascorbyl palmitate.

The tocopherol ester can be selected from the group consisting of tocopheryl acetate and tocopheryl propionate. Preferably, the tocopherol ester is tocopheryl acetate.

The skin cream composition of the present invention can further comprise additional, ancillary components whose use is optional but preferable. These ancillary components comprise:

(1) a solvent component;
(2) a preservative component;
(3) a thickener component;
(4) a hydrophilic component;
(5) a lipid-soluble component;
(6) octyl methoxycinnamate;
(7) aloe extract;
(8) benzophenone-3;
(9) pigment; and
(10) fragrance;

Preferably, the composition of the present invention comprises all of these ancillary components.

The solvent component can be selected from the group consisting of propylene glycol, 1,3-butylene glycol, and mixtures thereof. Preferably, the solvent component is 1,3-butylene glycol. Most preferably, the 1,3-butylene glycol comprises from about 3.4% to about 4.6% of the composition.

The preservative component can comprise at least one ingredient selected from the group consisting of:

(i) a complex consisting essentially of phenoxyethanol, methylparaben, ethylparaben, propylparaben, and butylparaben; and
(ii) a complex consisting essentially of propylene glycol, phenoxyethanol, chlorphenesin, and methylparaben. Preferably, the preservative component comprises both of these complexes. Most preferably, the complex consisting essentially of phenoxyethanol, methylparaben, ethylparaben, propylparaben, and butylparaben comprises from about 0.65% to about 0.85% of the composition and the complex consisting essentially of propylene glycol, phenoxyethanol, chlorphenesin, and methylparaben comprises from about 2.1% to about 2.9% of the composition.

The thickener component can comprise at least one of xanthan gum and carrageenan. Preferably, the thickener component comprises both xanthan gum and carrageenan, and the xanthan gum comprises from about 0.2% to about 0.3% of the composition and the carrageenan comprises from about 0.3% to about 0.5% of the composition.

The hydrophilic component can comprise a polar complex consisting essentially of mannitol, arginine, serine, pyrrolidone carboxylate, sucrose, citrulline, glycogen, histidine, alanine, threonine, glutamic acid, and lysine. Preferably, the polar complex comprises from about 4.25% to about 5.75% of the composition.

The lipid-soluble component can comprise at least one ingredient selected from the group consisting of:
(i) hydrogenated vegetable oil;
(ii) a long-chain fatty acid ester of glycerol selected from the group consisting of glyceryl stearate, glyceryl palmitate, and glyceryl arachidate;
(iii) an arachidyl ester of a short-chain fatty acid selected from the group consisting of arachidyl propionate, arachidyl acetate, arachidyl butyrate, and mixtures thereof;
(iv) a long-chain fatty acid ester of a medium-chain alcohol selected from the group consisting of octyl palmitate, octyl myristate, octyl stearate, heptyl palmitate, heptyl myristate, heptyl stearate, nonyl palmitate, nonyl myristate, nonyl stearate, and mixtures thereof;
(v) steareth-2;
(vi) cetyl alcohol;
(vii) steareth-21;
(viii) dimethicone;
(ix) jojoba oil;
(x) a myristyl ester of a long-chain fatty acid selected from the group consisting of myristyl myristate, myristyl laurate, myristyl palmitate and mixtures thereof;
(xi) bisabolol;
(xii) hydrogenated jojoba oil; and
(xiii) jojoba esters.

Preferably, the lipid-soluble component comprises hydrogenated vegetable oil, glyceryl stearate, arachidyl propionate, octyl palmitate, steareth-2, cetyl alcohol, steareth-21, dimethicone, jojoba oil, myristyl myristate, bisabolol, hydrogenated jojoba oil, and jojoba esters, and the hydrogenated vegetable oil comprises from about 1.5% to about 2% of the composition, the glyceryl stearate comprises from 0.5% to about 0.7% of the composition, the arachidyl propionate comprises from about 2.65% to about 3.65% of the composition, the octyl palmitate comprises from about 8.5% to about 11.5% of the composition, the steareth-2 comprises from about 1.275% to about 1.775% of the composition, the cetyl alcohol comprises from about 0.95% to about 1.30% of the composition, the steareth-21 comprises from about 1.275% to about 1.775% of the composition, the dimethicone comprises from about 0.4% to about 0.6% of the composition, the jojoba oil comprises from about 4.25% to about 5.75% of the composition, the myristyl myristate comprises from about 0.95% to about 1.3% of the composition, the bisabolol comprises from about 0.4% to about 0.6% of the composition, the hydrogenated jojoba oil comprises from about 0.75% to about 1.05% of the composition, and the jojoba esters comprise from about 0.75% to about 1.75% of the composition.

Preferably, the octyl methoxycinnamate comprises from about 2.1% to about 2.9% of the composition.

Preferably, the aloe extract comprises from 0.4% to about 0.6% of the composition.

Preferably, the benzophenone-3 comprises from about 2.1% to about 2.9% of the composition.

Preferably, the pigment comprises titanium dioxide and the titanium dioxide comprises from about 0.85% to about 1.15% of the composition.

Preferably, the fragrance comprises from about 0.25% to about 0.45% of the composition.

A preferred skin cream composition of the present invention comprises:
water, and emulsified and dispersed in the water:
(1) sodium lactate;
(2) a micellar complex comprising horse chestnut extract, Crataegus extract, water, panthenol, propylene glycol, phospholipids, phenoxyethanol, glycosphingolipids, chlorphenesin, and cholesterol, wherein the horse chestnut extract and the Crataegus extract each comprise from about 9% to about 18% of the micellar complex, the water comprises from about 24% to about 36% of the micellar complex, and the panthenol, the propylene glycol, the phospholipids, the phenoxyethanol, the glycosphingolipids, the chlorphenesin, and the cholesterol each comprise from about 3% to about 9% of the micellar complex;
(3) a protein complex comprising serum proteins, hydrolyzed collagen, glycerol, sodium lactate, sodium pyrrolidone carboxylate, and glycogen, wherein the serum proteins and the hydrolyzed collagen each comprises from about 20% to about 30% of the protein complex, the glycerol comprises from about 25% to about 35% of the protein complex, the sodium lactate comprises from about 5% to about 15% of the protein complex, the sodium pyrrolidone carboxylate comprises from about 5% to about 10% of the protein complex, and the glycogen comprises from about 2% to about 8% of the protein complex;
(4) a carbohydrate-based complex of dextran, glycine, and glucosamine, wherein the dextran comprises from about 70% to about 90% of the carbohydrate-based complex, the glycine comprises from about 10% to about 20% of the carbohydrate-based complex, and the glucosamine comprises from about 5% to about 15% of the carbohydrate-based complex;
(5) retinyl palmitate;
(6) ascorbyl palmitate;
(7) tocopheryl acetate;
(8) a complex of cyclomethicone and dimethiconol, wherein the cyclomethicone comprises about 87% of the complex and the dimethiconol comprises about 13% of the complex;
(9) an aqueous solution of sodium hyaluronate;
(10) glycosaminoglycans;
(11) a lipid complex of phospholipids, sphingolipids, and octyldodecanol, wherein the phospholipids comprise from about 2% to about 20% of the lipid complex, the sphingolipids comprise from about 0.01% to about 2% of the complex, and the octyldodecanol comprises from about 78% to about 97.99% of the complex;
(12) a solvent component;
(13) a preservative component;
(14) a thickener component;
(15) a hydrophilic component;
(16) a lipid-soluble component;

(17) octyl methoxycinnamate;
(18) aloe extract;
(19) benzophenone-3;
(20) pigment; and
(21) fragrance.

In this composition, the sodium lactate, the micellar complex, the protein complex, the carbohydrate-based complex, the retinyl palmitate, the ascorbyl palmitate, the tocopheryl acetate, the sodium hyaluronate solution, the complex of cyclomethicone and dimethiconol, the glycosaminoglycans, and the lipid complex are each present in a quantity sufficient to increase the smoothness and/or firmness of skin to which the composition is applied.

A particularly preferred skin cream composition of the present invention comprises:

water and emulsified and dispersed in the water:

(1) about 3.4% to about 4.6% of 1,3-butylene glycol;
(2) about 4.25% to about 5.75% of sodium lactate;
(3) about 0.2% to about 0.3% of carrageenan;
(4) A stabilizer complex consisting essentially of propylene glycol, phenoxyethanol, chlorphenesin, and methylparaben, wherein the propylene glycol comprises from about 40% to about 60% of the stabilizer complex, the phenoxyethanol comprises from about 30% to about 50% of the stabilizer complex, and the chlorphenesin and the methylparaben each comprise from about 15% to about 30% of the stabilizer complex;
(5) about 2.1% to about 2.9% of a polar complex consisting essentially of mannitol, arginine, serine, pyrrolidone carboxylate, sucrose, citrulline, glycogen, histidine, alanine, threonine, glutamic acid, and lysine wherein the mannitol, the arginine, the serine, the pyrrolidone carboxylate, the sucrose, the citrulline, the glycogen, the histidine, the alanine, the threonine each comprises from about 2% to about 20% of the polar complex, and the glutamic acid and the lysine each comprises from about 0.1% to about 2% of the polar complex;
(6) about 1.5% to about 2.0% of hydrogenated vegetable oil;
(7) about 0.5% to about 0.7% of glycerol stearate;
(8) about 2.65% to about 3.65% of arachidyl propionate;
(9) about 8.5% to about 11.5% of octyl palmitate;
(10) about 1.275% to about 1.75% of steareth-2;
(11) about 0.95% to about 1.3% of cetyl alcohol;
(12) about 1.275% to about 1.775% of steareth-21;
(13) about 0.4% to about 0.6% of dimethicone;
(14) about 4.25% to about 5.75% of jojoba oil;
(15) about 0.95% to about 1.3% of myristyl myristate;
(16) about 0.4% to about 0.6% of tocopheryl acetate;
(17) about 0.4% to about 0.6% of bisabolol;
(18) about 0.4% to about 0.6% of aloe extract;
(19) about 0.75% to about 1.05% of hydrogenated jojoba oil;
(20) about 0.75% to about 1.05% of jojoba esters;
(21) about 2.1% to about 2.9% of octyl methoxycinnamate;
(22) about 3% to about 4% of benzophenone-3;
(23) about 0.05% to about 0.15% of retinyl palmitate;
(24) about 0.01% to about 0.02% of ascorbyl palmitate;
(25) about 2% to about 5% of a lipid complex comprising phospholipids, sphingolipids, and octyldodecanol, wherein the phospholipids comprise from about 2% to about 20% of the lipid complex, the sphingolipids comprise from about 0.01% to about 2% of the lipid complex, and the octyldodecanol comprises from about 78% to about 97.99% of the complex;
(26) about 0.85% to about 1.15% of titanium dioxide;
(27) about 2.5% to about 3.5% of a micellar complex comprising horse chestnut extract, Crataegus extract, water, panthenol, propylene glycol, phospholipids, phenoxyethanol, glycosphingolipids, chlorphenesin, and cholesterol, wherein the horse chestnut extract and the Crataegus extract each comprise from 9% to about 18% of the micellar complex, water comprises from about 24% to about 36% of the micellar complex, and the panthenol, the propylene glycol, the phospholipids, the phenoxyethanol, the glycosphingolipids, the chlorphenesin, and the cholesterol each comprise from about 3% to about 9% of the micellar complex;
(28) about 2.5% to about 3.5% of a protein complex comprising serum proteins, hydrolyzed collagen, glycerol, sodium lactate, sodium pyrrolidone carboxylate, and glycogen, wherein the serum proteins and the hydrolyzed collagen each comprises from about 20% to about 30% of the protein complex, the glycerol comprises from about 25% to about 35% of the protein complex, the sodium lactate comprises from about 5% to about 15% of the protein complex, the sodium pyrrolidone carboxylate comprises from about 5% to about 10% of the protein complex, and the glycogen comprises from about 2% to about 8% of the protein complex;
(29) about 0.65% to about 0.85% of a complex consisting essentially of phenoxyethanol, methylparaben, ethylparaben, propylparaben, and butylparaben;
(30) about 0.25% to about 0.45% of fragrance;
(31) about 3.4% to about 4.6% of a 1% aqueous solution of sodium hyaluronate;
(32) about 2% to about 6% of glycosaminoglycans;
(33) about 0.0001% to about 0.1% of a complex of cyclomethicone and dimethiconol, wherein the cyclomethicone comprises about 87% of the complex and the dimethiconol comprises about 13% of the complex; and
(34) about 0.001% to about 0.1% of a carbohydrate-based complex comprising dextran, glycine, and glucosamine, wherein the dextran comprises from about 70% to about 90% of the carbohydrate-based complex, the glycine comprises from about 10% to about 20% of the carbohydrate-based complex, and the glucosamine comprises from about 5% to about 15% of the carbohydrate-based complex.

DESCRIPTION

A new combination of ingredients results in a skin cream that simultaneously promotes significant retexturizing of the skin, increasing its smoothness, improving its color, reducing age spots, while also increasing its firmness and moisture content.

The skin cream composition of the present invention comprises an aqueous base in which cosmetic components are emulsified and dispersed. The cosmetic components are:

(1) sodium lactate;
(2) a complex comprising horse chestnut extract, phospholipids, and glycosphingolipids;
(3) a complex comprising serum proteins and glycogen;
(4) a carbohydrate-based complex comprising dextran, glycine, and glucosamine;
(5) a long-chain fatty acid ester of retinol;
(6) a long-chain fatty acid ester of ascorbic acid; and (7) a short-chain fatty acid ester of tocopherol.

Preferably, the complex comprising horse chestnut extract, phospholipids, and glycosphingolipids is a micellar complex further comprising Crataegus extract, water, panthenol, propylene glycol, phenoxyethanol, chlorphenesin, and cholesterol.

Preferably, the complex comprising serum proteins and glycogen further comprises hydrolyzed animal proteins.

Preferably, the skin cream composition further contains additional, optional cosmetic components and ancillary components. The optional cosmetic components comprise:
(1) a complex of cyclomethicone and dimethiconol;
(2) an aqueous solution of sodium hyaluronate;
(3) glycosaminoglycans; and
(4) a lipid complex comprising phospholipids, sphingolipids, and octyldodecanol.

Typically, the composition of the present invention also comprises ancillary components such as:
(1) a solvent component;
(2) a preservative component;
(3) a thickener component;
(4) a hydrophilic component;
(5) a lipid-soluble component;
(6) octyl methoxycinnamate;
(7) aloe extract;
(8) benzophenone-3;
(9) pigment; and
(10) fragrance.

Preferably, the composition includes all of these ancillary components.

The ingredients are dispersed in an emulsified composition by the methods of preparation disclosed below. "Dispersed" refers to any process by which the ingredients are uniformly distributed in the emulsified base, and includes dissolving, emulsifying, and forming a colloidal suspension.

I. NATURE AND PROPORTION OF INGREDIENTS OF THE SKIN CREAM COMPOSITION

A. The Cosmetic Components

Each of the cosmetic components disclosed above contribute to the improved properties of the skin cream composition of the present invention and is present in a quantity sufficient to increase the smoothness and/or firmness of skin to which the composition is applied, as well as minimizing age spots.

Preferably, the composition further comprises optional cosmetic components including:
(1) a complex of cyclomethicone and dimethiconol;
(2) an aqueous solution of sodium hyaluronate;
(3) glycosaminoglycans; and
(4) a lipid complex comprising phospholipids, sphingolipids, and octyldodecanol.

Each of these components is also present in a quantity sufficient to increase the smoothness and/or firmness of skin to which the composition is applied; these components provide additional beneficial effects.

Preferred compositions for these cosmetic components, including the optional cosmetic components, are now disclosed. However, other compositions containing the required ingredients set forth above are possible.

1. The Protein Complex

The protein complex comprises serum proteins, hydrolyzed animal proteins, and glycogen. Although Applicant does not intend to be bound by this theory, it is believed that these components counteract the loss of essential ground substance due to the normal aging process. These components are believed to provide volume and bulk to result in a denser and firmer skin. Preferably, the protein complex further comprises sodium lactate, sodium pyrrolidone carboxylate, and glycerol.

Preferably, the serum proteins come from human serum, such as the albumin or globulin fractions. Preferably, the hydrolyzed animal protein comes from a source such as bovine, ovine, or porcine protein. Most preferably, the hydrolyzed animal protein is hydrolyzed collagen.

Preferably, the serum proteins and the hydrolyzed collagen each comprises from about 20% to about 30% of the protein complex, the glycerol comprises from about 25% to about 35% of the protein complex, the sodium lactate comprises from about 5% to about 15% of the protein complex, the sodium pyrrolidone carboxylate comprises from about 5% to about 10% of the protein complex, and the glycogen comprises from about 2% to about 8% of the protein complex.

Most preferably, the protein complex comprises from about 2.5% to about 3.5% of the skin cream composition.

An example of a suitable protein complex is Iconoderm LS 1054B, commercially available from Lab Serobiologique, Inc., Somerville, N.J.

2. The Micellar Complex

The micellar complex comprises horse chestnut extract, Crataegus (hawthorne blossom) extract, water, panthenol, propylene glycol, phospholipids, phenoxyethanol, glycosphingolipids, and cholesterol. The micellar complex provides significant hydration and moisturizing activities, as well as healing, soothing, calming, and anti-irritant activities. The micelles are colloidal vectors with an average particle size of less than 0.001 mm and are stable globular structures formed by lipids oriented such that their polar head groups are on the surface and their hydrocarbon tails are sequestered in the interior of the micelle. They are much smaller than any previously used "capsules" in cosmetics, e.g., liposomes, and can therefore penetrate the skin faster and to greater depth. They are also much more stable than liposomes and therefore much more effective.

Horse chestnut extract and Crataegus extract are plant extracts that are believed to exert anti-stress, anti-inflammatory, calming, and soothing effects.

Panthenol is the racemic dl-form of 2,4-dihydroxy-N-(3-hydroxypropyl)-3,3-dimethylbutanamide, and is also known as vitamin $B_5$. It is believed to exert a calming, soothing, and protective affect on the skin. The phospholipids can be phosphatidyl ethanolamine, phosphatidyl choline, phosphatidyl serine, phosphatidyl inositol, or diphosphatidyl glycerol.

Glycosphingolipids comprise ceramide covalently bound to carbohydrate on the primary hydroxyl group of the ceramide. The carbohydrate is typically glucose, lactose, N-acetylglucosamine, N-acetylglactosamine, or sialic acid.

The glycosphingolipids are believed to have a powerful hydrating affect, together with the ability to restructure and reinforce the barrier effect of the skin and improve the cohesion of the corneocytes. They are also believed to have an overall soothing effect and to exert a protective role against environmental aggression.

Preferably, the horse chestnut extract comprises from about 9% to about 18% of the micellar complex, the Crataegus extract comprises from about 9% to about 18% of the micellar complex, water comprises from about 24% to about 36% of the micellar complex, and the panthenol, the propylene glycol, the phospholipids, the phenoxyethanol, the glycosphingolipids, the chlorphenesin, and the cholesterol each comprise from about 3% to about 9% of the micellar complex. Preferably, the micellar complex comprises from about 2.5% to about 3.5% of the composition.

An example of a suitable micellar complex is Micelles Leniplex LS 6309, commercially available from Lab Serobiologique, Inc., Somerville, N.J.

3. Sodium Lactate

Another cosmetic component is sodium lactate. Preferably, sodium lactate comprises from about 4.25% to about 5.75% of the composition. A suitable form of sodium lactate is a complex of lactic acid and sodium hydroxide in which the lactic acid comprises from about 42% to about 58% of the complex and the sodium hydroxide comprises the remainder of the complex, approximately neutralizing the lactic acid.

4. The Carbohydrate-Based Complex

The carbohydrate-based complex comprises dextran, glycine, and glucosamine. Preferably, the dextran comprises from about 70% to about 90% of the complex, the glycine comprises from about 10% to about 20% of the complex, and the glucosamine is from about 5% to about 15% of the complex. Preferably, the complex of dextran, glycine, and glucosamine comprises from about 0.0001% to about 0.1% of the composition. A suitable complex of dextran, glycine, and glucosamine is Thalassamine LS 80/98, commercially available from Lab Serobiologique, Inc.

5. The Long-Chain Fatty Acid Ester of Retinol

An additional cosmetic component is a long-chain fatty acid ester of retinol. Preferably, the retinol ester is selected from the group consisting of retinyl palmitate, retinyl myristate, and retinyl stearate. Most preferably, the retinyl ester is retinyl palmitate. Preferably, the retinyl ester comprises from about 0.05% to about 0.15% of the skin cream composition of the present invention.

6. The Long-Chain Fatty Acid Ester of Ascorbic Acid

An additional cosmetic component is a long-chain fatty acid ester of ascorbic acid. Preferably, the ascorbic acid ester is ascorbyl palmitate. Preferably, the ascorbic acid ester comprises from about 0.01% to about 0.02% of the composition.

7. The Short-Chain Carboxylic Acid Ester of Tocopherol

An additional cosmetic component is a short-chain carboxylic acid ester of tocopherol. Preferably, the short-chain carboxylic acid ester of tocopherol selected from the group consisting of tocopheryl acetate and tocopheryl propionate. Most preferably, the tocopherol ester is tocopheryl acetate. Preferably, the tocopherol acetate comprises from about 0.4% to about 0.6% of the composition.

8. Optional Cosmetic components

The use of the following cosmetic components is optional, but preferred. They provide additional smoothness and/or firmness of the skin to which the composition is applied.

a. The Complex of Cyclomethicone and Dimethiconol

The composition preferably further comprises a complex of cyclomethicone and dimethiconol. Preferably, the cyclomethicone comprises about 87% of the complex and the dimethiconol comprises about 13% of the complex. Preferably, the complex of cyclomethicone and dimethiconol comprises from about 0.0001% to about 0.1% of the composition. A suitable complex is Dow Corning 1401 fluid (Dow Corning, Midland, Mich.).

b. Sodium Hyaluronate

The skin cream composition can further comprise an aqueous solution of sodium hyaluronate. Preferably, the aqueous solution is about 1% by weight, and the sodium hyaluronate solution comprises from about 3.4% to about 4.6% of the skin cream composition.

c. Glycosaminoglycans

The skin cream composition can further comprise glycosaminoglycans. These glycolipid derivatives contribute to the restoration of the ground substance of the skin. Preferably, the glycosaminoglycans comprise from about 2% to about 6% of the composition.

d. The Lipid Complex

The skin cream can further comprise a lipid complex comprising phospholipids, sphingolipids, and octyldodecanol. Preferably, the phospholipids comprise from about 2% to about 20% of the lipid complex, the sphingolipids comprise from about 0.01% to about 2% of the lipid complex, and octyldodecanol comprises from about 78% to about 97.99% of the lipid complex. Preferably, the lipid complex comprises from about 2% to about 5% of the composition. A suitable complex is Ceramides LS 2303, marketed by Lab Serobiologique, Inc.

Preferably, the skin cream composition comprises the complex of cyclomethicone and dimethiconol, the aqueous solution of sodium hyaluronate, glycosaminoglycans, and the lipid complex, in addition to the cosmetic components disclosed above.

B. The Ancillary Components

The ancillary components, whose use is optional but preferable, impart additional desirable properties to the skin cream composition of the present invention. These components can include:

(1) a solvent-component;
(2) a preservative component;
(3) a thickener component;
(4) a hydrophilic component;
(5) a lipid-soluble component;
(6) octyl methoxycinnamate;
(7) aloe extract;
(8) benzophenone-3;
(9) pigment; and
(10) fragrance;

Preferably, the composition of the present invention comprises all the ancillary components as indicated below.

1. The Solvent Component

The skin cream composition can comprise the solvent component for greater uniformity and ease of preparation. The solvent component can be selected from the group consisting of propylene glycol, 1,3-butylene glycol, and mixtures thereof. Preferably, the solvent component is 1,3-butylene glycol. Preferably, the 1,3-butylene glycol comprises from about 3.4% to about 4.6% of the composition.

2. The Preservative Component

The composition can further comprise a preservative component to retard microbial and mold growth in the composition, which is typically manufactured under clean but non-sterile conditions. The preservative component can comprise at least one ingredient selected from the group consisting of:

(1) a complex consisting essentially of phenoxyethanol, methylparaben, ethylparaben, propylparaben, and butylparaben; and (2) a complex consisting essentially of propylene glycol, phenoxyethanol, chlorphenesin, and methylparaben.

Preferably, the preservative component comprises both of these complexes.

Preferably, the complex consisting essentially of phenoxyethanol, methylparaben, ethylparaben, propylparaben, and butylparaben comprises from 0.65% to 0.85% of the composition. A suitable complex consisting essentially of phenoxyethanol, methylparaben, ethylparaben, propylparaben, and butylparaben is Phenonip™, available from Nipa Laboratories, Inc., Wilmington, Del. Phenonip™ is a practically colorless, viscous, liquid mixture of phenoxyethanol (60%–80%), methylparaben (13%–17%), ethylparaben (4%–6%), propylparaben (4%–6%), and butylparaben (4%–6%).

Preferably, the complex consisting essentially of propylene glycol, phenoxyethanol, chlorphenesin, and methylparaben comprises from about 2.1% to about 2.9% of the composition. Preferably, the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex. A suitable complex of propylene glycol, phenoxyethanol, chlorphenesin, and methylparaben is available as Stabilizer 388 from Lab Serobiologique, Inc.

3. The Thickener Component

The thickener component can comprise at least one of xanthan gum and carrageenan. Preferably, the thickener component comprises both xanthan gum and carrageenan. Most preferably, the xanthan gum comprises from about 0.2% to about 0.3% of the composition, and the carrageenan comprises from about 0.3% to about 0.5% of the composition.

4. The Hydrophilic Component

The skin cream composition can further comprises a hydrophilic component. Preferably, the hydrophilic component comprises a polar complex consisting essentially of mannitol, arginine, serine, pyrrolidone carboxylate, sucrose, citrulline, glycogen, histidine, alanine, threonine, glutamic acid, and lysine. A suitable polar complex is Hydratyl 8453, from Lab Serobiologique, Inc., which comprises from about 2% to about 20% each of mannitol, arginine, serine, pyrrolidone carboxylate, sucrose, citrulline, glycogen, histidine, alanine, and threonine, and from 0.1% to about 2% each of glutamic acid and lysine. Preferably, the polar complex comprises from about 4.25% to about 5.75% of the composition.

5. The Lipid-Soluble Component

The skin cream composition of the present invention can further comprise a lipid-soluble component to provide added smoothness. The lipid-Soluble component can comprise at least ingredient selected from the group consisting of:

(1) hydrogenated vegetable oil;

(2) a long-chain fatty acid ester of glycerol selected from the group consisting of glyceryl stearate, glyceryl palmitate, and glyceryl arachidate;

(3) an arachidyl ester of a short-chain fatty acid selected from the group consisting of arachidyl propionate, arachidyl acetate, arachidyl butyrate, and mixtures thereof;

(4) a long-chain fatty acid ester of a medium-chain alcohol selected from the group consisting of octyl palmitate, octyl myristate, octyl stearate, heptyl palmitate, heptyl myristate, heptyl stearate, nonyl palmitate, nonyl myristate, nonyl stearate, and mixtures thereof;

(5) steareth-2;

(6) cetyl alcohol;

(7) steareth-21;

(8) dimethicone;

(9) jojoba oil;

(10) a myristyl ester of a long-chain fatty acid selected from the group consisting of myristyl myristate, myristyl laurate, myristyl palmitate and mixtures thereof;

(11) bisabolol;

(12) hydrogenated jojoba oil; and

(13) jojoba esters.

Preferably, the lipid-soluble component comprises all of these ingredients.

Preferably, the long-chain fatty acid ester of glycerol is glyceryl stearate. Preferably, the arachidyl ester of the short-chain fatty acid is arachidyl propionate. Preferably, the long-chain fatty acid ester of the medium-chain alcohol is octyl palmitate. Preferably, the myristyl ester of the long-chain fatty acid is myristyl myristate.

Steareth-2 is polyoxyethylene (2) stearylether with 0.01% butylated hydroxyanisole and 0.005% citric acid added as preservatives. Similarly, steareth-21 is polyoxyethylene (21) stearylether with 0.01% butylated hydroxyanisole and 0.005% citric acid added as preservatives. Most preferably, the lipid-soluble component comprises hydrogenated vegetable oil, glyceryl stearate, arachidyl propionate, octyl palmitate, steareth-2, cetyl alcohol, steareth-21, dimethicone, jojoba oil, myristyl myristate, bisabolol, hydrogenated jojoba oil, and jojoba esters, wherein the hydrogenated vegetable oil comprises from about 1.5% to about 2% of the composition, the glyceryl stearate comprises from 0.5% to about 0.7% of the composition, the arachidyl propionate comprises from about 2.65% to about 3.65% of the composition, the octyl palmitate comprises from about 8.5% to about 11.5% of the composition, the steareth-2 comprises from about 1.275% to about 1.775% of the composition, the cetyl alcohol comprises from about 0.95% to about 1.30% of the composition, the steareth- 21 comprises from about 1.275% to about 1.775% of the composition, the dimethicone comprises from about 0.4% to about 0.6% of the composition, the jojoba oil comprises from about 4.25% to about 5.75% of the composition, the myristyl myristate comprises from about 0.95% to about 1.3% of the composition, the bisabolol comprises from about 0.4% to about 0.6% of the composition, the hydrogenated jojoba oil comprises from about 0.75% to about 1.05% of the composition, and the jojoba esters comprise from about 0.75% to about 1.75% of the composition.

6. Octyl Methoxycinnamate

The composition can further comprise octyl methoxycinnamate. Preferably, the octyl methoxycinnamate comprises from about 2.1% to about 2.9% of the composition.

7. The Aloe Extract

The composition can further comprise aloe extract. Preferably, the aloe extract comprises from 0.4% to about 0.6% of the composition.

8. Benzophenone-3

The composition can further comprise benzophenone-3, which exerts a protective effect by screening out ultraviolet rays. Preferably, the benzophenone-3 comprises from about 3% to about 4% of the composition.

9. The Pigment Component

The skin cream of the composition can further comprise a pigment component to give the skin cream an aesthetically desirable appearance. Preferably, the pigment component is titanium dioxide. Most preferably, the titanium dioxide comprises from about 0.85% to about 1.15% of the composition. Other pigments can be substituted for titanium dioxide depending upon the intended user.

10. The Fragrance

The skin cream composition of the present invention can further comprise fragrance. Preferably, fragrance comprises from about 0.25% to about 0.45% of the composition. The fragrance used is a conventional cosmetic fragrance chosen to impart the desired olfactory properties to the skin cream composition. The use of fragrance is well-known in the cosmetic art.

The preferred concentrations of both the cosmetic components and the ancillary components are shown in Table I. Also shown in Table I are the mixtures of which each component is a part for the preparation of the composition as discussed below.

II. PREPARATION OF THE SKIN CREAM COMPOSITION

The various mixtures and the sequences in which they are prepared and combined for the preparation of the skin cream composition of the present invention are now described in some detail. The mixtures can be combined in several orders, of which the following two disclosed below are representative but not exclusive. The object of the mixing sequence is to prepare a smooth and homogeneous composition as an emulsion.

A. First Mixing Sequence

Mixtures I (butylene glycol and lactic acid) and II (xanthan gum and carrageenan) are introduced into a stainless-steel kettle equipped with a high-speed mixer such as a Lightnin' TM mixer by sprinkling Mixture II into Mixture I. The combination of Mixture II and I are mixed vigorously for 30 minutes at room temperature until homogenous. Separately, Mixture III (the mineralized water) is introduced into a steam-jacketed stainless-steel AGI kettle large enough to hold the entire preparation and sweep mixing is begun at fast speed while heating to 70°-75° C. The combination of Mixtures I and II is added to Mixture III while maintaining temperature and mixing. Mixtures IV (the complex of propylene glycol, phenoxyethanol, chlorphenesin, and methylparaben) and V (the polar complex) are then added to the steam-jacketed stainless-steel kettle to which Mixtures I, II, and III have already been added. The combination of Mixtures I-V is then mixed vigorously with sweep mixing for 10 minutes at 70°-75° C. until homogenous. The temperature and mixing are maintained. Separately, Mixtures VI (the lipid-soluble components), VII (the octyl methoxycinnamate), and VIII (the benzophenone-3) are introduced into another steam-jacketed stainless-steel kettle equipped with a high-speed Mixture such as a Lightnin' TM mixture and heated to 70°-75° C. Vigorous mixing is begun when the bulk is sufficiently liquified. The temperature and mixing are maintained. Just before the combination of Mixtures I-V with Mixtures VI-VIII, add Mixture IX (retinol palmitate and ascorbyl palmitate) to Mixtures VI-VIII with vigorous mixing for five minutes. Mixtures VI-IX are then added at 70°-75° C. to the steam-jacketed stainless kettle containing Mixtures I-V at 70°-75° C. Fast speed homogenization mixing with slow sweep mixing is begun. Homogenization mixing is continued at 70°-75° C. for 30 minutes. The batch is then cooled at a rate of 1° C./3 minutes while maintaining mixing. Mixture X (the complex of phospholipids, sphingolipids, and octyldodecanol) is then added to the steam-jacketed stainless-steel kettle at 60°-65° C., and mixing is continued until homogeneous. The combination of Mixtures I-X is then cooled to 50°-55° C. Mixture XI (demineralized water) is charged into another stainless-steel kettle equipped with a high-speed mixer, and vigorous mixing is begun. Mixture XII (titanium dioxide) is added to Mixture XI with vigorous mixing until uniform. Immediately, the combination of Mixtures XI and XII are added to the batch kettle and mixed vigorously until uniform.

Mixture XIII (the micellar complex) is then charged into another stainless-steel kettle equipped with a high-speed mixer and vigorous mixing is begun. Mixture XIV (the protein complex) is added to Mixture XIII with vigorous mixing until uniform. The batch kettle is then cooled to 40°-45° C., and the combination of Mixtures XIII and XIV is added to the batch kettle with vigorous mixing until uniform. Mixtures XV (the complex consisting essentially of phenoxyethanol, methylparaben, ethylparaben, propylparaben, and butylparaben) and Mixture XVI (fragrance) are then added to the batch kettle at 40°-45° C. with vigorous mixing until uniform. The batch kettle is then cooled to 25°-30° C. Mixtures XVII (sodium hyaluronate), XVIII (glycosaminoglycans), and XIX (the complex of cyclomethicone and dimethiconol) are then added to the batch kettle. Mixture XX (the carbohydrate-based complex and the demineralized water, premixed) is then added to the batch kettle with mixing until uniform. Mixing is discontinued, and the prepared composition is filled into storage vessels for cold room storage at 18°-22° C.

B. Second Mixing Sequence

The second mixing sequence is identical to the first mixing sequence except that the combination of Mixtures I and II, mixed initially in a stainless-steel kettle equipped with a high-speed mixer, is not added to the batch kettle until after the combination of Mixtures IV-IX is added to the batch kettle. Thus, the batch kettle contains a combination of Mixtures III-IX, to which the combination of Mixtures I and II is then added. After the combination of Mixtures I and II is added to the batch kettle containing Mixtures III-IX, vigorous mixing is maintained for 30 minutes until the combination of Mixtures I-IX is uniform. Cooling of the batch is then begun at a rate 1° C./3 minutes while maintaining mixing, as in mixing sequence I. Mixture X is then added as before, and the rest of the additions are as in mixing sequence I.

TABLE I
INGREDIENTS OF A PREFERRED SKIN CREAM COMPOSITION ACCORDING TO THE PRESENT INVENTION

| Mixture | Components | Percentage Range |
|---|---|---|
| I | Butylene Glycol | 3.40-4.60 |
| I | Sodium Lactate | 4.25-5.75 |
| II | Xanthan Gum | 0.20-0.30 |
| II. | Carrageenan | 0.30-0.50 |
| III. | Demineralized Water | 23.25-31.50 |
| IV. | Complex of Propylene Glycol, Phenoxyethanol, Chlorphenesin, and Methylparaben | 2.10-2.90 |
| V. | Complex of Mannitol, Arginine, Serine, Pyrrolidone, Carboxylic Acid, Sucrose, Citrulline, Glycogen, Histidine, Alanine, Threonine, Glutamic Acid, and Lysine | 4.25-5.75 |
| VI. | Hydrogenated Vegetable Oil | 1.50-2.00 |
| VI | Glyceryl Stearate | 0.50-0.70 |
| VI | Arachidyl Propionate | 2.65-3.65 |
| VI | Octyl Palmitate | 8.50-11.50 |
| VI | Steareth-2 | 1.275-1.775 |
| VI | Cetyl Alcohol | 0.95-1.30 |
| VI | Steareth-21 | 1.275-1.775 |
| VI | Dimethicone | 0.40-0.60 |
| VI | Jojoba Oil | 4.25-4.75 |
| VI | Myristyl Myristate | 0.95-1.30 |
| VI | Tocopheryl Acetate | 0.40-0.60 |
| VI | Bisabolol | 0.40-0.60 |
| VI | Aloe Extract | 0.40-0.60 |
| VI | Hydrogenated Jojoba Oil | 0.75-1.05 |
| VI | Jojoba Esters | 0.75-1.05 |
| VII | Octyl Methoxycinnamate | 2.10-2.90 |
| VIII | Benzophenone-3 | 3.00-4.00 |
| IX | Retinyl Palmitate | 0.05-0.15 |
| IX | Ascorbyl Palmitate | 0.01-0.02 |
| X | Complex of Phospholipids, Sphingolipids, and Octyldodecanol | 2.00-5.00 |
| XI | Demineralized Water | 3.40-4.60 |
| XII | Titanium Dioxide | 0.85-1.15 |
| XIII | Micellar Complex of Horse Chestnut Extract, *Crataegus* Extract, Water, Panthenol, Propylene, Glycol, Phospholipids, Phenoxyethanol, Glycosphingolipids, Chlorphenesin, and Cholesterol | 2.50-3.50 |
| XIV | Complex of Glycerol, Hydrolyzed Collagen, Serum Proteins, Sodium Lactate, Sodium Pyrrolidone Carboxylate, and Glycogen | 2.50-3.50 |
| XV | Complex of Phenoxyethanol, Methylparaben, Ethylparaben, Propylparaben, and Butylparaben | 0.65-0.85 |
| XVI | Fragrance | 0.25-0.45 |
| XVII | Sodium Hyaluronate, 1% Aqueous Solution | 3.40-4.60 |

TABLE I-continued
INGREDIENTS OF A PREFERRED SKIN CREAM COMPOSITION ACCORDING TO THE PRESENT INVENTION

| Mixture | Components | Percentage Range |
|---|---|---|
| XVIII | Glycosaminoglycans | 2.00-6.00 |
| XIX | Complex of Cyclomethicone and Dimethiconol | 0.0001-0.10 |
| XX | Complex of Dextran, Glycine, and Glucosamine | 0.0001-0.10 |
| XX | Demineralized Water | 0.85-1.15 |

ADVANTAGES OF THE INVENTION

The skin cream composition of the present invention provides significantly improved retexturization of the skin, giving significantly improved smoothness, as well as significantly minimizing age spots, improving color, together with increasing the firmness and moisture content of the skin. The composition is suitable for prolonged and repeated use.

Although the present invention has been described in considerable detail with regard to certain preferred versions thereof, other versions are possible. Therefore, the spirit and scope of the appended claims should not be limited to the descriptions of the preferred versions contained herein.

I claim:

1. A skin cream composition comprising: water, and dispersed in the water:
   (a) about 4.25% to about 5.75% of sodium lactate;
   (b) about 2.5% to about 3.5% of a complex comprising horse chestnut extract, phospholipids, and glycosphingolipids;
   (c) about 2.5% to about 3.5% of a complex comprising serum proteins and glycogen;
   (d) about 0.001% to about 0.1% of a carbohydrate-based complex comprising dextran, glycine, and glucosamine;
   (e) about 0.05% to about 0.15% of a long-chain fatty acid ester of retinol selected from the group consisting of retinyl palmitate, retinyl myristate, and retinyl stearate;
   (f) about 0.01% to about 0.02% of ascorbyl palmitate; and (g) about 0.4% to about 0.6% of a short-chain carboxylic acid ester of tocopherol selected from the group consisting of tocopheryl acetate and tocopheryl propionate; the sodium lactate, the complex comprising horse chestnut extract, phospholipids, and glycosphingolipids, the complex comprising serum proteins and glycogen, the carbohydrate-based complex, the retinyl ester, the ascorbyl palmitate, and the tocopheryl ester each being present in a quantity sufficient to increase the smoothness and/or firmness of skin to which the composition is applied.

2. The skin cream composition of claim 1 wherein the complex comprising horse chestnut extract, phospholipids, and glycosphingolipids is a micellar complex further comprising Crataegus extract, water, panthenol, propylene glycol, phenoxyethanol, chlorphenesin, and cholesterol, wherein the horse chestnut extract and the Crataegus extract each comprise from about 9% to about 18% of the micellar complex, the water comprises from about 24% to 36% of the micellar complex, and the panthenol, the propylene glycol, the phospholipids, the phenoxyethanol, the glycosphingolipids, the chlorphenesin, and the cholesterol each comprise from about 3% to about 9% of the micellar complex.

3. The skin cream composition of claim 1 wherein the complex comprising serum proteins and glycogen further comprises hydrolyzed animal proteins.

* * * * *